United States Patent
Pampaloni et al.

(10) Patent No.: US 9,816,916 B2
(45) Date of Patent: Nov. 14, 2017

(54) CAPILLARY CELL, ARRANGEMENT AND METHOD FOR ACCOMMODATING, POSITIONING AND EXAMINING A MICROSCOPIC SPECIMEN

(71) Applicant: Johann Wolfgang Goethe-Universitaet, Frankfurt am Main (DE)

(72) Inventors: Francesco Pampaloni, Frankfurt Am Main (DE); Ernst H. K. Stelzer, Meckesheim (DE); Christian Mattheyer, Frankfurt Am Main (DE)

(73) Assignee: Johann Wolfgang Goethe-Universitaet, Frankfurt am Main (DE)

( * ) Notice: Subject to any disclaimer, the term of this patent is extended or adjusted under 35 U.S.C. 154(b) by 317 days.

(21) Appl. No.: 14/425,259

(22) PCT Filed: Sep. 3, 2013

(86) PCT No.: PCT/EP2013/068186
§ 371 (c)(1),
(2) Date: Mar. 2, 2015

(87) PCT Pub. No.: WO2014/033320
PCT Pub. Date: Mar. 6, 2014

(65) Prior Publication Data
US 2015/0211981 A1    Jul. 30, 2015

(30) Foreign Application Priority Data
Sep. 3, 2012 (DE) .................. 10 2012 108 158

(51) Int. Cl.
*G01N 1/00* (2006.01)
*G01N 21/03* (2006.01)
(Continued)

(52) U.S. Cl.
CPC ............ *G01N 21/03* (2013.01); *B01L 3/5082* (2013.01); *G01N 21/11* (2013.01); *G01N 21/13* (2013.01);
(Continued)

(58) Field of Classification Search
CPC .. G01N 33/54386; G01N 33/86; G01N 15/06; G01N 15/1434; G01N 1/10;
(Continued)

(56) References Cited

U.S. PATENT DOCUMENTS 3,867,042 A * 2/1975 Mayer .................... G01N 21/05
250/576
5,690,895 A   11/1997 Matsumoto et al.
(Continued)

FOREIGN PATENT DOCUMENTS

DE     2156688 A1    5/1972
DE     2613582 A1    10/1977
(Continued)

OTHER PUBLICATIONS

International search report from PCT/EP2013/068186 dated Nov. 4, 2013.
(Continued)

*Primary Examiner* — Michael P Stafira
(74) *Attorney, Agent, or Firm* — Marsall, Gerstein & Borun LLP (57) ABSTRACT

A capillary cell is described along with an arrangement and a method for receiving, positioning and examining a microscopic specimen, in particular a cleared fluorescent specimen with the help of a single-plane fluorescence microscope. The capillary cell is suitable for being positioned in a chamber volume and contains a capillary section, which comprises a wall. The wall encloses a specimen volume and is planar and transparent in at least some sections. In
(Continued)

addition, the capillary cell includes an upper and a lower closure section, which are connected to the capillary section and which seal the capillary section. The specimen volume is separated from the chamber volume by the capillary section, the upper closure section and the lower closure section.

22 Claims, 4 Drawing Sheets

(51) Int. Cl.

| | |
|---|---|
| *B01L 3/00* | (2006.01) |
| *G01N 21/11* | (2006.01) |
| *G01N 21/64* | (2006.01) |
| *G01N 21/13* | (2006.01) |
| *G02B 21/16* | (2006.01) |
| *G02B 21/00* | (2006.01) |
| *G02B 21/26* | (2006.01) |
| *G02B 21/33* | (2006.01) |

(52) U.S. Cl.
CPC ..... *G01N 21/6458* (2013.01); *G01N 21/6486* (2013.01); *G02B 21/16* (2013.01); *B01L 2300/042* (2013.01); *B01L 2300/0858* (2013.01); *G01N 21/0303* (2013.01); *G01N 2021/0307* (2013.01); *G01N 2021/0346* (2013.01); *G01N 2021/0378* (2013.01); *G01N 2021/0389* (2013.01); *G01N 2201/025* (2013.01); *G01N 2201/06113* (2013.01); *G02B 21/0076* (2013.01); *G02B 21/26* (2013.01); *G02B 21/33* (2013.01)

(58) Field of Classification Search
CPC .. G01N 1/14; G01N 1/28; G01N 1/36; G01N 2001/149; G01N 2001/368; G01N 2015/0693; G01N 2021/0346; G01N 2021/6439; G01N 21/251
See application file for complete search history.

(56) References Cited

U.S. PATENT DOCUMENTS

| | | | | |
|---|---|---|---|---|
| 5,818,578 A | * | 10/1998 | Inman | C23C 16/4412 356/246 |
| 5,949,537 A | * | 9/1999 | Inman | G01N 21/031 356/246 |
| 6,017,765 A | * | 1/2000 | Yamada | G01N 27/44721 204/602 |
| 6,473,171 B1 | | 10/2002 | Buttry et al. | |
| 6,542,231 B1 | * | 4/2003 | Garrett | G01N 21/05 250/227.11 |
| 2003/0086086 A1 | * | 5/2003 | Kerschmann | G01N 21/03 356/244 |
| 2008/0123091 A1 | * | 5/2008 | Yamamoto | G01N 21/0303 356/244 |
| 2008/0212073 A1 | * | 9/2008 | Ehring | G01N 21/05 356/51 |
| 2009/0208072 A1 | | 8/2009 | Seibel | |
| 2010/0067104 A1 | | 3/2010 | Lippert et al. | |
| 2010/0177305 A1 | | 7/2010 | Chen | |

FOREIGN PATENT DOCUMENTS

| | | |
|---|---|---|
| DE | 2844004 A1 | 4/1980 |
| DE | 3226407 A1 | 1/1984 |
| DE | 8902144 U1 | 5/1989 |
| DE | 19612487 A1 | 10/1997 |
| DE | 19616571 A1 | 10/1997 |
| DE | 69221423 T2 | 3/1998 |
| DE | 69316778 T2 | 9/1998 |
| DE | 69324614 T2 | 12/1999 |
| DE | 69621151 T2 | 11/2002 |
| DE | 69714355 T2 | 4/2003 |
| DE | 69334085 T2 | 5/2007 |
| DE | 102006028516 B3 | 10/2007 |
| DE | 60037628 T2 | 12/2008 |
| DE | 102007048409 A1 | 4/2009 |
| DE | 102008027784 A1 | 12/2009 |
| DE | 202010017281 U1 | 6/2011 |
| DE | 202010017827 U1 | 11/2012 |
| EP | 075605-1 A | 4/1983 |
| EP | 1171761 A1 | 1/2002 |
| EP | 1192007 A1 | 4/2002 |
| EP | 1489404 A1 | 12/2004 |
| EP | 1493826 B1 | 1/2005 |
| EP | 2599548 A1 | 6/2013 |
| JP | S62-269042 A | 11/1987 |
| JP | H03-108641 A | 5/1991 |
| JP | H06-281558 A | 10/1994 |
| JP | 2010-164565 A | 7/2010 |
| JP | 2011-013167 A | 1/2011 |
| JP | 2011-512543 A | 4/2011 |

OTHER PUBLICATIONS

Pampaloni, et al. "The third dimension bridges the gap between cell culture and live tissue," Nature Reviews Molecular Cell Biology, 8:839-845 (2007).
International Preliminary Report on Patentability for International Application No. PCT/EP2013/068186, dated Mar. 12, 2015.
List of Cited References cited in German Application No. 102012108158.1 (2015).
Office Action from Japanese Patent Application No. 2015-529063 dated Apr. 21, 2017.

* cited by examiner

CAPILLARY CELL, ARRANGEMENT AND METHOD FOR ACCOMMODATING, POSITIONING AND EXAMINING A MICROSCOPIC SPECIMEN

FIELD OF THE INVENTION

The present invention is in the field of specimen preparation and specimen positioning for microscopy. In particular it relates to a capillary cell and an arrangement containing the capillary cell as well as a method for receiving, positioning and examining a fluorescent, cleared microscopic specimen with the help of a fluorescence microscope (epifocal, confocal and light sheet illumination microscopes).

RELATED PRIOR ART

For examination of biological or medical specimens, fluorescence microscopy is used in the state of the art. In medical research, fluorescence microscopy is used, for example, to observe the effects (e.g., the toxicity) of a certain substance on a specimen.

The specimens used include, among others, cell cultures, certain embryos, for example, the embryos of roundworms, zebra fish or mice, and biopsies.

In fluorescence microscopy the structures to be examined are typically labeled with a fluorescent dye. Another possibility is to use specimens that already contain certain fluorescent dyes.

In order to be able to record images of fluorescence microscopic specimens, the specimens must be illuminated with light of a certain wavelength, which results in excitation of the fluorescent dye. Due to the excitation, the fluorescent dye emits fluorescent light, whose wavelength in general deviates from the wavelength of the exciting illuminating light.

With the help of a microscope, the fluorescent light can be detected and thus the specimen structures that have been labeled with the fluorescent dye can be visualized. To image only the specimen structures from a certain specimen plane and to mask out those from other specimen levels and/or layers, the specimens can be illuminated locally in one plane, so that only structures from the illuminated specimen plane are excited to emission of fluorescent light. As a result of the selective light sheet illumination, the microscopic image of the fluorescent light therefore shows only specimen structures of the illuminated plane. This is referred to as light sheet fluorescence microscopy.

To obtain a three-dimensional representation of fluorescent specimen structures, the light sheet can be shifted relative to a stationary specimen or the specimen can be shifted relative to a stationary single plane. The fluorescent images from various specimen layers can then be combined into a three-dimensional representation of the corresponding specimen structure.

To obtain the sharpest possible images of the specimen structure, the fluorescent light emitted from the interior of the specimen should be scattered as little as possible within the specimen. One possibility is to use specimens that are naturally transparent, such as small fish embryos, for example. Another possibility is to make the specimen transparent by a special method of brightening ("clearing"), without thereby destroying the specimen structures to be investigated.

For such clearing, the specimen is first dehydrated and then placed in a clearing medium. The clearing medium penetrates into the specimen and makes the refractive index of the intracellular and extracellular constituents approximately the same. As a result light passing through the specimen is scattered much less, so the specimen becomes transparent. The specimen is usually dehydrated with alcohol. The clearing medium, in which the specimen is placed after dehydration, has a high refractive index, which is suitable for the biological specimen. These media are usually apolar—and therefore water-soluble—solvents, which is why the specimen is normally dehydrated first. A typical clearing medium consists of one part benzyl alcohol and two parts benzyl benzoate (abbreviation: BABB).

After the fluorescent specimen has been cleared, it can be examined with the help of a fluorescence microscope, for example, a light sheet fluorescence microscope. Instead of a light sheet fluorescence microscope, other types of fluorescence microscopes may also be used, for example, epifocal or confocal fluorescence microscopes. In light sheet microscopy, the specimen is normally placed in a chamber, which is filled with an immersion medium. The immersion medium has a high refractive index, which prevents a divergence of the fluorescent light on emerging from the specimen and/or on exit from a medium in which the specimen is embedded. The immersion medium permits a higher resolution of the specimen images.

The recording and/or positioning of the specimen within the chamber is often very complicated. Another problem is that the immersion medium, which is in the chamber, may come in contact with the specimen and may have a negative effect on the clearing. In the article "Ultramicroscopy Reveals Axonal Transport Impairments in Cortical Motor Neurons at Prion Disease," Ermolayev et al., Biophysical Journal, Vol. 96, 3390-3398, April 2009, it is reported that a specimen for a fluorescence microscopic examination was mounted on a glass rod using an acrylamide adhesive. The specimen was positioned inside a chamber by shifting the glass rod.

Another possibility for recording a specimen and positioning a specimen for examination under a microscope is described in US Patent Application 2010/0067104 A1. US 2010/0067104 A1 discloses a specimen holder, which is situated in a chamber that can be filled with an immersion fluid. The specimen is embedded in an agarose gel cylinder which has a greater solidity than the immersion medium surrounding the agarose gel cylinder. The agarose cylinder is connected to the specimen container and is at least partially in contact with the immersion medium in its examination. With the help of a moving stage and another drive, the agarose gel cylinder together with the specimen can be positioned relative to a detection lens.

The known devices and methods for recording, positioning and examining cleared microscopic fluorescent specimens allow three-dimensional representations to be recorded but they are subject to a few disadvantages. For example, the clearing of the specimen can be impaired by the immersion medium. In addition, the recording of specimens in the state of the art is quite complex.

Furthermore there is no known method of recording in the state of the art that is suitable for an examination of viable microscopic specimens.

SUMMARY OF THE INVENTION

The present invention is based on the object of making available a device and a method for an improved recording, positioning and examination of specimens without the disadvantages mentioned above.

This object is achieved by a capillary cell, by an arrangement, and by a method as claimed.

The capillary cell according to the invention comprises a capillary section and a top closure section and a bottom closure section, which are connected to the capillary section. The capillary section comprises a wall, which is planar and transparent in at least some sections. The wall surrounds a specimen volume. The capillary cell is suitable for being positioned in a chamber volume. The capillary section is sealed by the top and bottom closure sections, so that the specimen volume is separated from the chamber volume.

The capillary cell according to the invention offers a number of advantages for recording and examining a cleared microscopic fluorescent specimen.

Due to the fact that the specimen volume is separated from the chamber volume, the specimen can be embedded in a certain specimen medium, which is different from the immersion medium within the chamber volume. This separation between specimen volume and chamber volume is of great practical importance. For example, the specimen volume may contain toxic substances with which the specimen is to be treated. In addition, the specimen volume may contain a toxic organic solution for adjusting the refractive index. Propagation of these toxic substances into the comparatively large and open chamber volume is not desirable and is prevented by the separation. Many smaller amounts of the corresponding substance are also needed to adjust a certain concentration within the specimen volume.

However, the separation prevents not only the specimen medium from escaping but also prevents the immersion medium of the chamber volume from coming in contact with the specimen. For example, the clearing of the specimen that is embedded in a clearing medium within the specimen volume might otherwise be affected negatively by the immersion medium. The capillary cell according to the invention prevents this negative effect and thus ensures a long-lasting specimen clearing and high imaging quality.

It can be concluded in general that the separation of the specimen volume and the chamber volume makes it possible at all to perform immersion recordings of a specimen that is in a specimen-specific environment, which can be adjusted as desired regardless of the immersion medium.

Another advantage of the self-contained specimen volume is that the site of retention of the specimen is limited to the specimen volume. This prevents the specimen from diffusing away and being lost in the chamber volume. This is advantageous in particular in investigating viable specimens which cannot move out of the specimen volume in an examination with the capillary cell according to the invention.

The capillary cell according to the invention also has a positive effect on the image quality. Curved transitional surfaces between different media in the beam path of the fluorescent light to be detected or in the illumination beam path lead to optical distortion. This optical distortion has a negative effect on the image quality. The fluorescent light of the specimen can exit the capillary cell without distortion due to the fact that, with the capillary cell according to the invention, the wall of the capillary section is planar and transparent in at least some sections. Thus, highly resolved and realistic specimen images can be recorded with a minimum of aberrations using the capillary cell according to the invention.

The wall, which is planar and transparent in at least some sections is also advantageous for a local fluorescence excitation of a single-plane to be illuminated. Based on the planar and transparent wall, the illuminating beam is not distorted and the local excitation may take place much more precisely than is the case with illumination through curved surfaces.

The capillary cell according to the invention is suitable in particular for examination of specimens using a light microscope, whose axes of illumination and detection are at a right angle to one another and/or using a light sheet fluorescence microscope or an epifocal or confocal fluorescence microscope.

The aforementioned connection between the upper and/or lower closure section and the capillary section is preferably releasable. In this case the capillary section has an upper and/or a lower opening which can be sealed by the upper and/or lower closure sections. To introduce the specimen into the specimen volume, the specimen may first be placed on the closure section, for example, with the help of a pipette or a micromanipulator. Next, the capillary section may be joined to the lower sealing section and the specimen may be introduced thereby into the specimen volume. Another possibility is to introduce the specimen into the specimen volume through the upper opening of the capillary section.

In an advantageous embodiment, the capillary cell comprises an inlet and an outlet. For example, the specimen to be analyzed may be introduced into the specimen volume through the inlet. In addition, media may also be delivered to the specimen volume through the inlet for the specimen treatment. Similarly, such a medium may also be removed from the specimen volume through the outlet. The supply of the medium through the inlet and its removal through the outlet respectively may also take place simultaneously, so that a flow is created inside the specimen volume. The flow can be used to center the specimen, as described below.

With the help of the inlet and the outlet, the ambient conditions of the specimen can be adjusted or altered precisely and as desired. This adjustment and/or change in the specimen environment can also be carried out during the investigation without having to remove the specimen. The inlet and outlet are preferably also situated in different closure sections, for example, the inlet being situated in the upper closure section and the outlet being situated in the lower closure section or vice versa. The flow in the longitudinal direction of the capillary section can be generated in this way.

The capillary cell preferably comprises a first and a second planar wall section. These two wall sections are facing in different directions so that both the illumination of the specimen and also the detection of the fluorescent light can take place without distortion in the corresponding directions. Fluorescent light emanating from the specimen passes from the specimen through the first planar wall section of the capillary cell and excitation light enters the capillary cell through the second planar wall section.

In a preferred embodiment, the capillary section of the capillary cell has a polygonal, in particular a quadratic or octagonal cross section. These cross-sectional shapes are especially advantageous. On the one hand, the fluorescent light emanating from the specimen can leave the capillary section in different directions through planar wall sections. Therefore, in a corresponding rotation of the capillary cell—the specimen can be imaged with a high quality in various perspectives. On the other hand, the specimen can also be illuminated precisely and locally in the various aforementioned perspectives through planar wall sections. The specimen can be illuminated in particular from directions which deviate from the direction of detection.

For example, in the case of a regular octagonal cross section, the illumination and detection take place at a right angles to one another and through planar wall sections. If the capillary section with the octagonal cross section together with the specimen is rotated, high-resolution images can be observed through the corresponding planar wall sections for eight different specimen perspectives. For each of the eight specimen perspectives, the specimen is illuminated through a corresponding planar wall section in particular. Neither the direction of detection nor the illumination need be altered.

The specimen is preferably restricted to a small specimen volume, in particular to a small lateral region, so that the internal cross-sectional area of the capillary section is preferably ≤10 mm$^2$ and especially preferably ≤7 mm$^2$.

However, the cross-sectional area should not be infinitely small, so that larger specimen volumes can also be examined accordingly. Furthermore, a sufficient specimen volume must be able to supply and maintain a defined specimen environment. The internal cross-sectional area of the capillary section is therefore preferably ≥0.1 mm$^2$ and especially preferably ≥0.2 mm$^2$.

It has been found that these ranges represent an optimum compromise between the strongest possible specimen restriction, a sufficiently large specimen volume, simple handling and good manufacturability.

The wall thickness of the capillary section is preferably ≤200 μm and especially preferably ≤100 μm and/or preferably ≥30 μm and especially preferably ≥50 μm. The inventors have recognized that these ranges offer an ideal compromise between manufacturability and stability of the capillary cell as well as low optical aberration.

To be able to align the capillary cell more easily for the examination, the capillary section preferably has a regular polygonal cross-sectional area. The angles between neighboring side surfaces of the capillary section preferably differ very little from one another. The angles deviate from their mean value by less than ±0.5°, especially preferably less than ±0.2°.

In an advantageous embodiment, the wall of the capillary section consists of a gas-permeable membrane in at least some sections. The concentration of a dissolved gas (e.g., oxygen or $CO_2$) and/or the pH within the specimen volume can therefore be adjusted or altered according to the gas concentration outside of the capillary cell. A defined specimen environment can therefore be created easily or the specimen environment can be altered in a defined manner. Furthermore, the monitoring and observation of the gas concentration are greatly simplified. For example, the oxygen concentration or the $CO_2$ concentration inside the capillary cell can be determined by measurement outside of the capillary cell.

The wall of the capillary cell is preferably made of high-quality optical glass in at least some sections. The optical glass preferably has a high uniformity of the refractive index. For example, the Schott N-F45 variety of glass is suitable; it has a refractive index n of n>1.46 and/or of n<1.52. The image quality can therefore be increased further because scattering effects and distortion effects are further reduced.

In an advantageous embodiment of the capillary cell, the surface of the wall is treated in at least some sections. The treatment may be that the surface is provided with mirrorization, for example, and/or with a blocking filter or band-elimination filter layer and/or with an antireflective coating. The coating may be applied in a sputtering or vapor deposition process, in a sol-gel process or an electroplating process. Interfering reflections, for example, of fluorescent light from the specimen on the wall regions of the capillary cell can be reduced by the antireflective coating, and the creation of mirror images of the specimen can be reduced. Certain wavelength ranges of the fluorescent light can be masked out by the blocking filter layer or the excitation of the specimen may not be excited for certain wavelength ranges.

Therefore, a specimen in which various structures are prepared with various fluorescent dyes, for example, can be examined selectively with respect to a certain structure. In addition, the detection of scattered light is minimized by the blocking filter layer. Due to the mirrorized surface of a wall section of the capillary cell, the adjustment of the illuminating laser beam can be simplified and the illuminating beam can be aligned perpendicular to or approximately perpendicular to a wall section of the capillary cell.

In addition, it is advantageous if the wall of the capillary cell has a mark to be able to position the capillary cell more easily within the chamber volume. With the help of the mark, the capillary cell can be shifted easily and quickly to a predetermined reference position. The reference position can be indicated optically for example, with a positioning laser.

For centering and fixation of the specimen within the capillary cell, the capillary cell preferably comprises a specimen centering mechanism. The specimen-centering mechanism is preferably arranged in the region of the lower sealing section. The specimen-centering device has a self-centering function, by means of which the specimen is centered as it is lowered within the capillary cell. The specimen is passively centered by the specimen centerer because of the force of gravity. Active centering is not necessary. This corresponds to the principle of kinematic positioning.

To improve the kinematic positioning of the specimen, a directed flow and/or a stream by means of which a force is exerted on the specimen is created within the capillary cell—as described above. By means of this force, the specimen is fixed at an observation site with the help of the specimen-centering mechanism. The kinematic positioning is especially advantageous for examination of viable specimens which could move freely in the specimen volume without the kinematic positioning.

The specimen-centering device preferably includes guide means having at least one guide surface and/or guide edge. The guide surface and/or guide edge is inclined toward the longitudinal axis of the capillary section and runs radially toward an observation site. In this way a specimen moving toward the observation site in the longitudinal direction of the capillary section—for example, due to the force of gravity or a flow—is guided in the radial direction toward the observation site by the guide surface and/or the guide edge. The guide surface and/or the guide edge acts like a skewed plane, which deflects a specimen movement in a longitudinal direction of the capillary section at least partially into a radial movement. The direction of radial movement is perpendicular to the longitudinal direction and to the wall of the capillary section. At the observation site, a further movement of the specimen in longitudinal direction is prevented geometrically, so that the specimen remains centered at the observation site based on the forces acting on it.

In an advantageous embodiment, the guide means has at least one first recess which is arranged in such a way that light emanating from the observation site passes through the first recess and can emerge from the capillary section through the respective aforementioned first planar wall section. The first recess ensures that the fluorescent light emanating from the specimen can be picked up at least partially without distortion and is not blocked completely by the guide means or is not distorted by the planar wall sections.

The guide means preferably also have at least one second recess. The second recess is arranged in such a way that light illuminating the observation site through the second aforementioned planar wall section can pass through the second recess. This ensures that the specimen can be illuminated adequately and without distortion, despite being centered in the specimen-centering device.

In addition, the invention relates to an arrangement for positioning a microscopic specimen. The arrangement comprises a capillary cell according to one of the embodiments described above and a moving stage, wherein the capillary cell can be connected to the moving stage, in particular with the help of a magnetic connection. On the one hand, the capillary cell can be attached securely, quickly and with a strong enough connection to the moving stage. On the other hand, the connection can be released rapidly and easily, so that the capillary cell can be removed without any complex renovation measures, for example, for replacement of the specimen or for a change in the specimen environment. The capillary cell can be positioned inside the chamber with the help of the moving stage, in particular being rotated about its longitudinal axis and/or displaced in the XYZ direction.

In addition, the invention comprises an arrangement for positioning and examining a microscopic specimen, in particular a cleared fluorescent specimen with the help of a light sheet fluorescence microscope. This arrangement comprises the aforementioned arrangement for positioning and also a chamber. The chamber consists of a chamber wall, which is transparent in at least some sections and which defines the aforementioned chamber volume. The moving stage is arranged together with the capillary cell at least partially inside the chamber volume, so that a specimen for an examination can be positioned within the chamber volume.

The chamber volume can be filled with an immersion fluid, for example, with water. Since the chamber wall is transparent in at least some sections, fluorescent light emitted from the specimen can leave the chamber and be picked up outside of the chamber. With the help of the moving stage, the capillary cell and thus the specimen can be positioned inside the chamber. The positioning may consist of a rotation and/or a displacement in any direction in space. Since the capillary cell is self-contained, the chamber volume is separated from the specimen volume. Due to this separation, there cannot be any negative effect on the specimen due to the immersion medium. Furthermore, this prevents the immersion medium from being contaminated or poisoned by the specimen medium.

The chamber wall preferably includes a first window and a second window. The specimen that is situated inside the capillary cell can be illuminated and excited to fluorescence through the first window. The fluorescent light emanating from the specimen can exit the chamber through the second window and be picked up outside of the chamber. The windows preferably face the observation site from different directions. This ensures that the fluorescent light detected does not overlap with the significantly more intense illumination light. This has the advantage that no additional filter is needed to free the fluorescent light detected of the illumination light.

The present invention additionally comprises a method for introducing a microscopic specimen into a capillary cell according to one of the embodiments described above. To do so, the specimen is first placed on the lower closure section, for example, using a pipette or a micromanipulator. Then the lower closure section is connected to the capillary section. To do so, the specimen is introduced into the specimen volume through the lower opening in the capillary section and the capillary cell is sealed. When the specimen-centering device is situated on the lower sealing section, the specimen can also be placed directly on the specimen-centering device in this process step before the capillary cell is closed with the lower closure section.

Alternatively the specimen may also be introduced into the capillary cell through the upper opening in the capillary section. To do so, the upper closure section of the closed capillary cell is removed and the specimen is introduced into the specimen volume or filled therein—optionally together with a specimen medium. Next the capillary section is again connected to the upper sealing section and the capillary cell is closed.

Another alternative consists of introducing the specimen through the inlet into the specimen volume. This alternative embodiment can also be used with capillary cells according to the invention with which the connection between the capillary section and the closure sections is not releasable and with which the closure sections are permanently connected to the capillary section.

In the method according to the invention, the specimen is preferably centered inside the capillary cell after being introduced into the specimen volume—and before being examined. The centering then takes place in that the specimen is moved in the longitudinal direction of the capillary section toward the observation site, based on a flow or a stream of the specimen medium or based on the force of gravity, wherein the specimen is guided toward the observation site in the radial direction with the help of the guide means of the specimen-centering device. The flow can then be generated as described previously.

In an advantageous embodiment, the method according to the invention additionally comprises introduction of a medium for treatment of the specimen. Herein, the medium for treatment of the specimen is introduced through the inlet. This introduction of medium may take place before or during the examination of the specimen. If the introduction takes place during the examination, it is for example possible to examine the effect of a change in the specimen environment on the specimen.

In addition, the invention relates to a method for examining a cleared microscopic fluorescent specimen using the arrangement described previously and with the help of a light sheet fluorescence microscope. The method comprises the steps of positioning the fluorescent specimen, illuminating the fluorescent specimen and detecting fluorescent light.

Herein, the fluorescent specimen is positioned with the help of the moving stage which rotates the capillary cell about its longitudinal axis and/or displaces it in the XYZ direction. The fluorescent specimen is illuminated through the first window, so that the fluorescent specimen is excited to fluorescence. The fluorescent light originating from the specimen is detected outside of the chamber behind the second window. The directions of illumination and of detection differ from one another so that a more intense illumination light is not superimposed on the fluorescent light detected. The illumination lens and the detection lens may be positioned along the corresponding optical axes with a high precision using lens guides. Accordingly, a shift of the focal plane, which is caused by a change in the spatial distribution of the refractive index in the chamber, can be compensated.

The present invention additionally comprises a method, which consists of any combination of the aforementioned methods.

BRIEF DESCRIPTION OF THE FIGURES

Additional advantages and features of the invention become apparent from the following description, in which the invention is explained in greater detail on the basis of preferred exemplary embodiments with reference to the accompanying drawings, in which:

FIGS. 1a), b) show a schematic perspective view of two different embodiments of the capillary cell according to the invention, FIGS. 2a)-c) show schematic perspective views of three different embodiments of a specimen-centering device.

DESCRIPTION OF PREFERRED EMBODIMENTS

Figure 1:
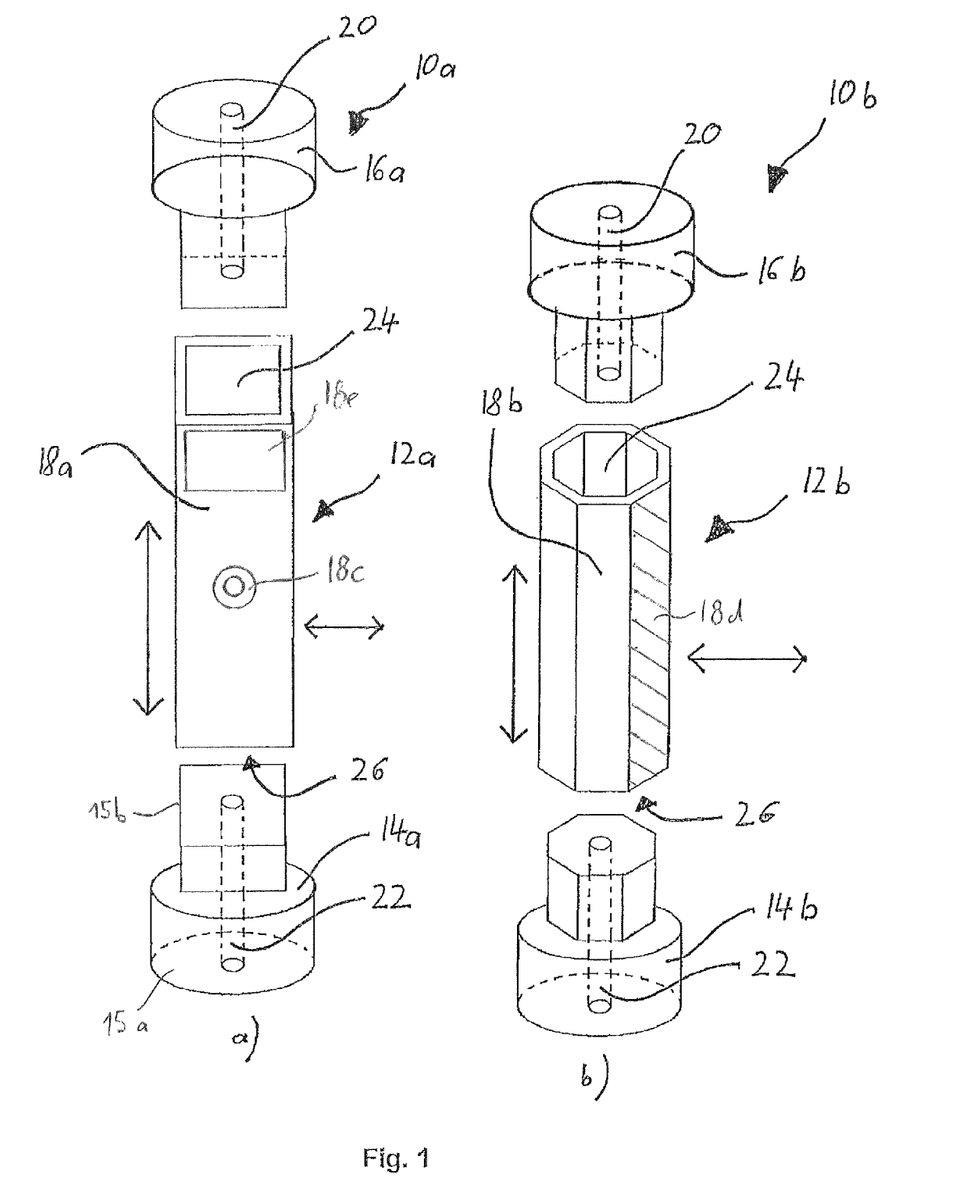

FIGS. 1 a) and b) show a schematic perspective view of two embodiments of the capillary cell according to the invention 10a, 10b. The capillary cell 10a, 10b comprises a capillary section 12a, 12b, a lower closure section 14a, 14b and an upper closure section 16a, 16b. The capillary section 12a, 12b comprises a wall 18a, 18b, which encloses a specimen volume. The upper closure section 16a, 16b comprises an inlet 20, and the lower closure section 14a, 14b comprises an outlet 22. The capillary section 12a, 12b has an upper opening 24 and a lower opening 26, which can be closed with the upper closure section 16a, 16b and/or with the lower closure section 14a, 14b. The wall 18a, 18b is transparent and is preferably made of optical glass so that a specimen (not shown), which is inside the capillary section 12a, 12b can be illuminated and excited to fluorescence. The fluorescent light emitted by the specimen can exit the capillary cell 10a, 10b through the transparent wall 18a, 18b.

The embodiment of the capillary cell 10a shown in FIG. 1a) comprises a capillary section 12a with a quadratic cross section. The wall 12a thus comprises four planar side surfaces through which a specimen inside the capillary cell 10a can be observed and examined in four different specimen views. To do so, the detection direction can be adjusted accordingly with a stationary capillary cell 10a, or the detection direction can be maintained and the capillary cell 10a can be rotated accordingly. In the exemplary embodiment in FIG. 1a), the angles of rotation then correspond to multiples of 90°. For the examination in each of the four specimen perspectives, the fluorescent light leaving the capillary section 12a at a 90° angle to the direction of illumination is detected. In the examination in each of the four specimen perspectives, the specimen is illuminated through a planar side surface. The fluorescent light to be detected thus passes through a neighboring planar side surface of the capillary section 12a.

The capillary cell 10b shown in FIG. 1b) contains a capillary section 12b with an octagonal cross section. Accordingly, the capillary section 12b has eight planar side surfaces. A specimen inside the capillary section 12b can therefore be observed through the respective planar side surfaces for eight different specimen perspectives. Because of the octagonal cross section, fluorescent light leaving the capillary section 12b at an angle of 45° or 90° to the direction of illumination is preferably detected in the case of the capillary cell 10b.

A medium can be supplied to the specimen volume through the inlet 20, and a medium can be removed from the specimen volume through the outlet 22. A flow or stream in the longitudinal direction can be created within the specimen volume (represented by a vertical double arrow in FIG. 1a) and in FIG. 1b)) by simultaneous supply and discharge. The radial direction in FIG. 1a) and FIG. 1b) is represented by a horizontal double arrow.

Figure 3:
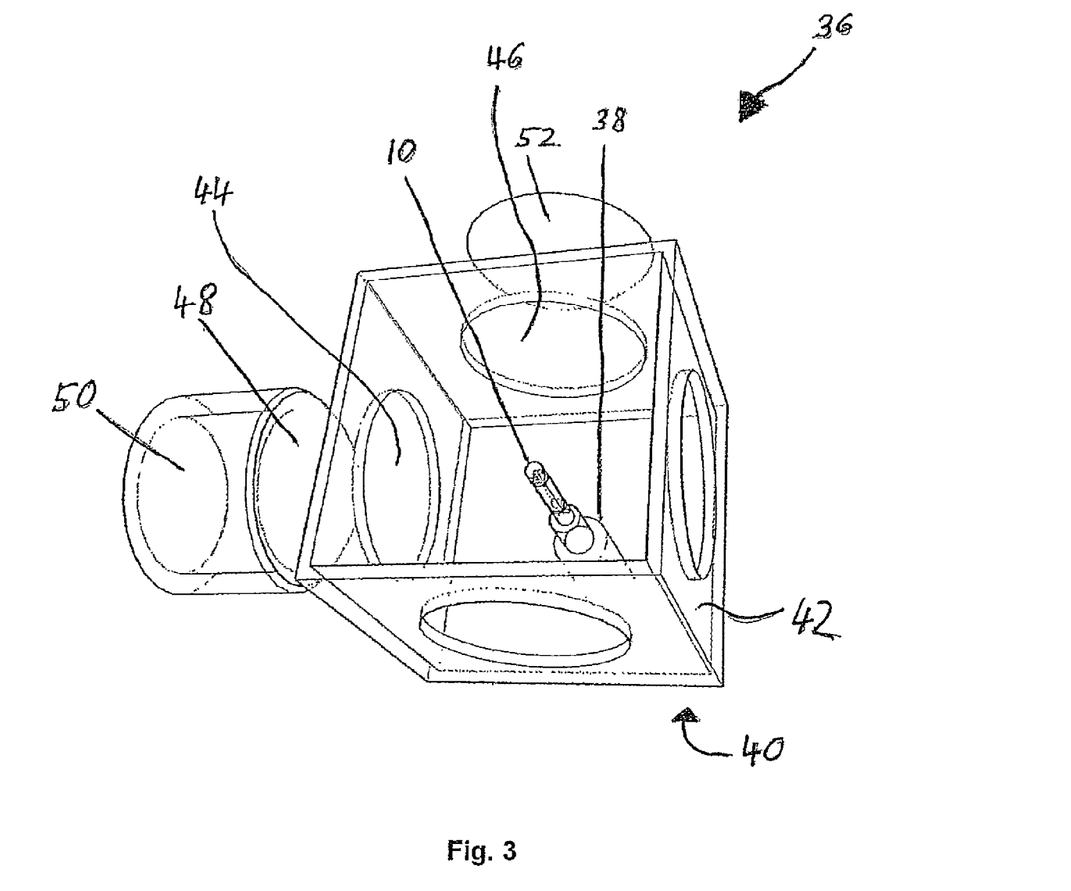
FIG. 3 shows a schematic perspective view of an arrangement according to the invention for recording, positioning and examining a specimen.

With further reference to FIG. 1a), on the wall 18a of the capillary section 12a, a marking 18c is provided for positioning the capillary cell 10a within a chamber volume of chamber 40 shown in FIG. 3. Moreover, the wall 18a comprises a section 18e which is formed by a gas-permeable membrane.

With reference to FIG. 1b), a section 18d of the wall 18b is provided with a mirrorization, indicated by a hatching in the drawing. Note that instead of the mirrorization, in alternative embodiments a blocking filter layer or an anti-reflective coating may be provided on section 18d of the wall 18b.

With reference again to FIG. 1a), the lower closure section 14a is shown to have a lower portion 15a and an upper portion 15b. In some embodiments, the lower portion 15a can be magnetic, such as to form a magnetic connection with a moving stage as shown under reference number 38 in FIG. 3.

Figure 2:
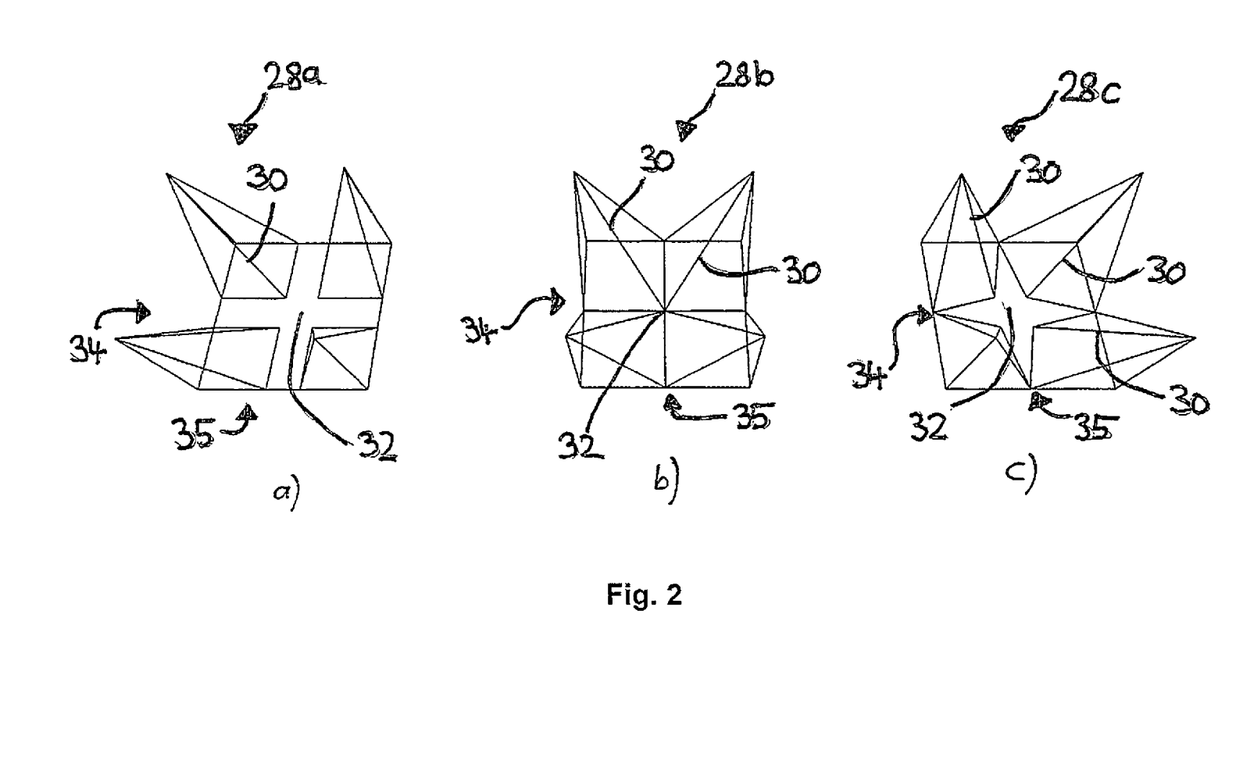

FIGS. 2a)-c) show three embodiments of a specimen-centering device 28a, 28b, 28c, with which a specimen (not shown) can be centered in the capillary cell 10. The specimen-centering devices 28a, 28b, 28c from FIG. 2 comprise guide means, each having four guide edges 30. The specimen-centering devices 28a, 28b, 28c are arranged in the capillary cell 10 in such a way that the guide edges 30 are inclined to the longitudinal axis (vertical double arrows in FIGS. 1a), b)) of the capillary section 12a, 12b, and in the radial direction (horizontal double arrows in FIG. 1) they converge to an observation site 32. The specimen-centering devices 28a, 28b, 28c also contain four recesses, including a first recess 34 and a second recess 35.

The first recess 34 allows fluorescent light that is emitted by a specimen at the specimen site 32 to leave the capillary cell 10 without the fluorescent light being refracted, scattered or blocked by the guide means. The second recess 35 allows the specimen at the specimen site 32 to be illuminated without any negative effect of the guide means on the illumination. Due to the fact that the first recess 34 and the second recess 35, as seen from the specimen site 32, face in different directions, fluorescent light whose direction deviates from the direction of the illuminating light accordingly can be detected. The detected fluorescent light is therefore not superimposed on the illumination light, thereby greatly simplifying detection.

The specimen-centering devices 28a, 28b, 28c shown in FIGS. 2a)-c), each having four recesses, are preferably used in the capillary cell 10a with a quadratic cross section of the capillary section 12a. The specimen-centering devices 28a, 28b, 28c that are shown can be arranged in the capillary cell 10a in such a way that a respective planar side surface is situated behind each of the four recesses, as seen from the specimen site 32. Illumination and detection through planar side surfaces are thus not impaired by the guide means. The terms "first recess" and "second recess" in the present description relate to the fluorescent light detected and the illumination, respectively. When the capillary cell 10a is used with one of the specimen-centering devices 28a, 28b, 28c in stationary detection and illumination, and the capillary cell 10a is rotated, then the terms "first" and "second" recess are switched between the four recesses as a function of the instant angle of rotation.

For other cross-sectional shapes of the capillary section 12, the specimen-centering device 28 is preferably adjusted accordingly, so that a corresponding recess of the specimen-centering device 28 can be assigned to each planar side surface of the capillary section 12.

The specimen-centering device 28a, 28b, 28c may be arranged on the lower closure part 14 for example. If the lower closure part 14 is connected to the capillary section 12 and a specimen medium with a specimen is introduced through the upper opening 24 of the capillary section 12 into the specimen volume, then the specimen drops onto the observation site 32 because of the force of gravity in the longitudinal direction of the capillary section 12. As soon as the specimen comes in contact with one of the four guide edges 30, the specimen is guided to the observation site 32 in the radial direction. For the centering, the specimen however need not necessarily be guided to the observation site 32 through the force of gravity. The specimen can also be moved to the observation site 32 by a flow in the longitudinal direction of the capillary section, so that the specimen is centered at the observation site 32 and fixed there. This type of centering and/or fixation is referred to in the following disclosure as "kinematic positioning."

FIG. 3 shows an arrangement 36 for recording, positioning and examining a cleared microscopic specimen. The arrangement 36 comprises a capillary cell according to the invention 10, a moving stage 38 and chamber 40. The chamber 40 comprises a chamber wall 42, which defines a chamber volume. The capillary cell 10 is connected to the moving stage 38 and is arranged inside the chamber volume. The chamber wall 42 also comprises a first window 44 and a second window 46. The first and second windows 44, 46 are each facing the capillary cell 10 and the observation site 32 from different directions. In addition, FIG. 3 shows an illumination lens 48, a lens slide 50 and a detection lens 52.

The specimen, which is situated in the capillary cell 10, can be illuminated through the first window 44 and excited to fluorescence. Fluorescent light emitted by the specimen can exit the chamber 40 through the second window 46 and can be detected with the help of the detection lens 52. To examine the specimen for different specimen views, the capillary cell 10 is rotated about its longitudinal axis with the help of the moving stage 38. The directions of detection and illumination remain preferably essentially stationary. Since the wall 18 of the capillary cell 10 has planar transparent side surfaces, the capillary cell 10 may be aligned in such a way that a planar transparent side surface is facing the first and second windows 44, 46. Therefore, on the one hand, fluorescent light that has passed exclusively through planar surfaces can be picked up. On the other hand, the specimen can be illuminated locally with sharp differentiation from other fluorescence-labeled specimen regions. This makes it possible to record distortion-free images of specimen structures with a high resolution.

The illumination and detection are offset by 90° from one another in the arrangement 36 from FIG. 3, so that the detected fluorescent light is not superimposed on more intense illumination light. An immersion medium for recording images with an increased numeric aperture can be introduced into the chamber volume. Therefore, the resolution can be increased. To do so, preferably a small distance is selected between the capillary cell 10 and the detection lens 52. For this purpose, the chamber wall 42 can also be indented in the direction of the capillary cell 10 in some sections so that the detection lens 52 can also be brought much closer to the capillary cell 10 than shown in FIG. 3.

To examine cell clusters three-dimensionally, the cell clusters can be cleared depending on the size and transparency to minimize scattering of the fluorescent light and the excitation light within the specimen. By shifting the capillary cell 10 along the direction of detection with the help of the moving stage 38, the illumination is also shifted within the specimen. Therefore fluorescent substances of another specimen plane are selectively excited to fluorescence. The fluorescent image thus recorded then corresponds to the structures from another plane of the specimen. By shifting the specimen through the illumination beam and assembling the images thereby recorded, it is possible to create a three-dimensional representation of the specimen structure.

Figure 4:
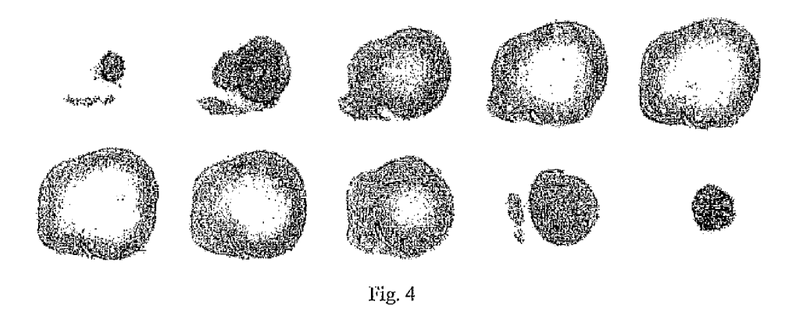
FIG. 4 shows negative specimen plane recordings of a fluorescent-labeled breast tumor cell cluster recorded with an arrangement according to the invention.

FIG. 4 shows recorded images from different specimen planes of a cell cluster consisting of cells from a breast tumor, comprising approximately 10,000 cells. The recorded images were recorded with the arrangement (36) according to the invention and inverted. Due to this inversion, the fluorescent regions appear dark in FIG. 4—as in FIGS. 5 and 6—and conversely, the regions that were originally light appear dark. The structural protein actin was labeled with the fluorescent dye phalloidin AF488 and the cell nuclei were labeled with the fluorescent dye Draq 5 for the recorded images. On the whole ten recorded images from different specimen depths are shown in FIG. 4, where the planar distance between two recorded images that are represented as adjacent to one another horizontally amounts to approximately 50 µm. The length of the black horizontal scaling bar in FIG. 4 is 50 µm. It can be seen here that the first three recorded images from the right in the upper row and the first three recorded images from the left in the lower row have non-fluorescent regions in the interior. These regions can be attributed to the fact that the corresponding cells in the nucleus of the cell cluster have died due to a lack of nutrients and gas exchange. This leaves only the cell fragments that do not contain any comparable fluorescent cell nuclei structure that are comparable to those of the outer cells.

Figure 5:
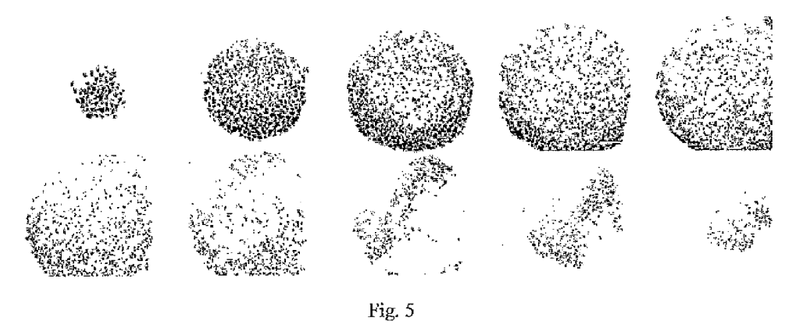
FIG. 5 shows negative planar specimen recordings of a cell cluster having fluorescent-labeled cell nuclei recorded with an arrangement according to the invention.
Figure 6:
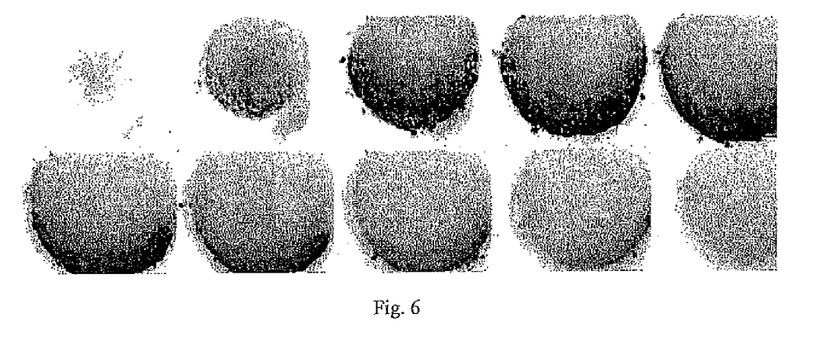
FIG. 6 shows negative planar specimen images of the cell cluster from FIG. 5, wherein the cell cluster has been cleared for the examination.

FIGS. 5 and 6 each show ten recorded images of a specimen from different specimen depths. The specimen examined is a cell cluster whose cell nuclei were labeled with the fluorescent dye Draq 5. The planar spacing between two horizontally adjacent recorded images that are shown here amounts to approximately 40 µm. Both of the recorded image sequences from FIG. 5 and FIG. 6 were performed using the arrangement 36 according to the invention. In contrast with the specimen from FIG. 5, the specimen from FIG. 6 was cleared for the examination.

Comparison of FIG. 5 with FIG. 6 shows clearly the advantage of a clearing of the fluorescent specimen examined. The cell nuclei from deeper specimen layers, which are in the interior of the specimen can be recorded distinctly in the cleared specimen in FIG. 6. In FIG. 5 however the fluorescent light of these cell nuclei—inasmuch as the illuminating light reaches the cell nuclei at all—does not reach the specimen surface due to the scattering in the interior of the specimen. Therefore, these cell nuclei are not imaged in FIG. 5.

For the examination of cleared specimens as shown in FIG. 6, the capillary cell 10 according to the invention is especially advantageous: during the examination, the specimen can be inserted within the specimen volume into a special clearing solution—for example, a mixture of benzyl alcohol and benzyl benzoate—to adjust the refractive index. Outside of the specimen volume, the chamber volume however may be filled with an aqueous immersion solution. Based on the separation of the specimen volume and the chamber volume, water immersion lenses may be used. Furthermore the specimen—which has been dehydrated for clearing—is not rehydrated by the aqueous immersion solution. Thus an optimal specimen clearing can also be maintained with the capillary cell 10 for long-term investigations lasting any length of time.

Another advantage is that water can be used as the immersion medium for recorded images having a large numeric aperture. The separation prevents the clearing solution, which is harmful to health, from escaping from the specimen volume into the chamber volume and mixing with the immersion solution. Therefore, the cleared specimen can be examined not only with improved resolution but also in a manner that is safe from the standpoint of the health of the experimenter at the same time, without having the clearing medium attack the lenses. Since the clearing media can cause severe damage to the lenses, air is often selected as the immersion medium between the specimen and the objective lens so that the light collection of light is comparatively minor. With the capillary cell according to the present invention, however, objectives with improved light-collecting properties may be used and the objects can be protected from damage at the same time.

It should be pointed out that FIGS. 4 through 6 serve only as examples of the use of the present invention but should by no means be limited to the applications that are described in detail. For example, it is also possible to examine viable specimens, which are examined within a specimen-specific culture medium, with the help of the capillary cell 10 according to the invention.

The exemplary embodiments that are illustrated in the drawings and described in detail in the preceding description are to be regarded as purely exemplary but not restricting the invention in any way. It should be pointed out that only the preferred exemplary embodiments are shown and described and all variations and modifications that might lie within the scope of protection of the present invention either at the present time or in the future are intended to be protected. The features that are presented may be important in any combination.

LIST OF REFERENCE NUMERALS 10a, b capillary cell
12a, b capillary section
14a, b lower sealing section
15a lower portion of lower sealing section
15b upper portion of lower sealing section
16a, b upper sealing section
18a, b wall
18c marking
18e, d wall sections
20 inlet
22 outlet
24 upper opening
26 lower opening
28a, b, c specimen-centering device
30 guide edge
32 observation site
34 first recess
35 second recess
36 arrangement for receiving, positioning and examining a microscope specimen
38 moving stage
40 chamber
42 chamber wall
44 first window
46 second window
48 illumination lens
50 lens slider
52 detection lens

The invention claimed is:

1. A capillary cell for receiving a microscopic specimen, wherein the capillary cell is suitable for being positioned in a chamber volume and comprises:
   a capillary section, which comprises a wall that encloses a specimen volume, wherein the wall is planar and transparent in at least some sections;
   an upper and a lower closure section, which are connected to the capillary section and seal it so that the specimen volume is separated from the chamber volume; and
   a specimen-centering device which contains a guide means having at least one guide surface and/or guide edge which is inclined with respect to the longitudinal axis of the capillary section and tapers radially to an observation site such that a specimen moving toward the observation site in the longitudinal direction of the capillary section is guided in a radial direction toward the observation site by guidance of the guide surface and/or the guide edge.

2. The capillary cell according to claim 1, wherein the aforementioned connection between the upper and/or lower closure sections and the capillary section is releasable, wherein the capillary section has an upper opening and/or a lower opening, which can be sealed by the upper closure section and/or the lower closure section.

3. The capillary cell according to claim 1, the capillary cell comprising an inlet and an outlet,
   wherein a specimen is introduced into the specimen volume through the inlet and/or a medium can be supplied to the specimen volume there through, and
   wherein a medium can be removed from the specimen volume through the outlet.

4. The capillary cell according to claim 3, wherein the inlet is arranged in the lower closure section and the outlet is arranged in the upper closure section or the inlet is arranged in the upper closure section and the outlet is arranged in the lower closure section.

5. The capillary cell according to claim 1, wherein the capillary section has at least one first and at least one second planar wall section, wherein fluorescent light emanating from the specimen can escape from the capillary cell through the first planar wall section, and wherein the specimen can be illuminated through the second planar well section.

6. The capillary cell according to claim 1, wherein the capillary section has a polygonal, in particular a quadratic or octagonal cross section.

7. The capillary cell according to claim 6, wherein the capillary section has an internal cross-sectional area which is ≥0.1 mm$^2$, and ≤10 mm$^2$.

8. The capillary cell according to claim 1, wherein the capillary section has a wall thickness which is ≥30 µm and ≤200 µm.

9. The capillary cell according to claim 6, wherein the angles between neighboring side surfaces of the capillary section deviate from their mean value by less than ±0.5°.

10. The capillary cell according to claim 1, wherein the wall consists of a gas-permeable membrane in at least some sections.

11. The capillary cell according to claim 1, wherein the wall consists of high-quality optical glass in at least some sections, said glass having a refractive index n of n >1.46 and of n <1.52.

12. The capillary cell according to claim 1, wherein the surface of the wall is treated in at least some sections, in particular being provided with a mirrorization and/or with a blocking filter layer and/or with an anti-reflective coating.

13. The capillary cell according to claim 1, wherein the wall has a marking for positioning the capillary cell within the chamber volume.

14. The capillary cell according to claim 1, wherein the specimen-centering device is arranged in the region of the lower closure section.

15. The capillary cell according to claim 1, wherein the guide means has at least one first recess, which is arranged so that light emanating from the observation site can pass through the first recess and can emerge from the capillary section through the aforementioned first planar wall section, and
wherein the guide means has at least one second recess, which is arranged so that light illuminating the observation site through the aforementioned second planar wall section can pass through the second recess.

16. An arrangement for positioning a microscopic specimen, wherein the arrangement comprises a capillary cell and a moving stage,
said capillary cell comprising
a capillary section, which comprises a wall that encloses a specimen volume, wherein the wall is planar and transparent in at least some sections, and
an upper and a lower closure section, which are connected to the capillary section and seal it so that the specimen volume is separated from the chamber volume,
wherein the capillary cell can be connected to said moving stage,
wherein the moving stage is suitable for positioning the capillary cell, and wherein the arrangement further comprises:
a chamber comprising a chamber wall that is transparent in at least some sections, wherein the chamber wall defines a chamber volume,
wherein the capillary cell is arranged at least partially inside said chamber volume,
wherein the moving stage is suitable for positioning the capillary cell at least partially inside the chamber volume, and
wherein the chamber is suitable for being filled with an immersion medium, and the capillary cell is suitable for being filled with a specimen medium.

17. The arrangement according to claim 16, wherein the chamber wall contains a first window through which a specimen situated in the capillary cell can be illuminated, and
wherein the chamber wall contains a second window through which fluorescent light which is emitted by a specimen inside the capillary cell can exit from the chamber,
wherein the windows are arranged so that they are not facing the observation site from opposite directions.

18. A method for introducing a microscopic specimen into a capillary cell, said capillary cell comprising a capillary section, which comprises a wall that encloses a specimen volume, wherein the wall is planar and transparent in at least some sections, and an upper and a lower closure section, which are connected to the capillary section and seal it so that the specimen volume is separated from the chamber volume, wherein the method comprises:
depositing the specimen on the lower closure section; and
connecting the capillary section to the lower closure section, wherein the specimen is introduced into the specimen volume through the lower opening in the capillary section.

19. The method according to claim 18, wherein the specimen volume contains a specimen medium and the microscopic specimen is centered due to a movement to the observation site based on a flow of the specimen medium or based on the force of gravity in the longitudinal direction of the capillary section,
wherein the specimen is guided in a radial direction to the observation site with the help of the guide means.

20. The method according to claim 18, which additionally comprises an introduction of a medium for a treatment of the specimen, wherein the medium for the specimen treatment is introduced into the specimen volume through an inlet and the introduction takes place before or during an optical examination of the specimen.

21. A method for examining a cleared microscopic fluorescent specimen with the help of a light sheet fluorescence microscope and using an arrangement comprising
a chamber comprising a chamber wall that is transparent in at least some sections, wherein the chamber wall defines a chamber volume,
a capillary cell comprising
a capillary section, which comprises a wall that encloses a specimen volume, wherein the wall is planar and transparent in at least some sections,
an upper and a lower closure section, which are connected to the capillary section and seal it so that the specimen volume is separated from the chamber volume,
a moving stage suitable for positioning said capillary cell at least partially inside the chamber volume, said chamber being filled with an immersion medium,
wherein the method comprises:
positioning the fluorescent specimen with the help of the moving stage within the chamber volume,
illuminating the fluorescent specimen through the first window, so that the fluorescent specimen is excited to fluorescence due to the illumination and emits fluorescent light in the direction of the second window,
detecting fluorescent light originating from the specimen, wherein the detection direction is different from the illumination direction and in particular is perpendicular to the illumination direction.

22. The capillary cell according to claim 6, wherein the angles between neighboring side surfaces of the capillary section deviate from their mean value by less than ±0.2°.

* * * * *

UNITED STATES PATENT AND TRADEMARK OFFICE
CERTIFICATE OF CORRECTION

PATENT NO. : 9,816,916 B2
APPLICATION NO. : 14/425259
DATED : November 14, 2017
INVENTOR(S) : Francesco Pampaloni et al.

Page 1 of 1

It is certified that error appears in the above-identified patent and that said Letters Patent is hereby corrected as shown below:

On the Title Page

At item (74), Line 1, "Marsall," should be -- Marshall, --.

In the Claims

At Column 14, Line 60, "well" should be -- wall --.

Signed and Sealed this
Fifteenth Day of May, 2018

Andrei Iancu
*Director of the United States Patent and Trademark Office*